US008299116B2

(12) United States Patent
Rubino et al.

(10) Patent No.: US 8,299,116 B2
(45) Date of Patent: *Oct. 30, 2012

(54) CCI-779 CONCENTRATE FORMULATIONS

(75) Inventors: Joseph T Rubino, Towaco, NJ (US); Victoria Siskavich, Lyon Mountain, NY (US); Maureen M Harrison, Sugar Loaf, NY (US); Pooja Gandhi, Highland Mills, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/206,641

(22) Filed: Aug. 10, 2011

(65) Prior Publication Data

US 2011/0294845 A1 Dec. 1, 2011

Related U.S. Application Data

(62) Division of application No. 10/626,943, filed on Jul. 25, 2003, now Pat. No. 8,026,276.

(60) Provisional application No. 60/399,526, filed on Jul. 30, 2002.

(51) Int. Cl.
*A61K 31/435* (2006.01)

(52) U.S. Cl. ........ 514/450; 514/454; 514/338; 514/294; 514/885; 514/970

(58) Field of Classification Search ........................ None
See application file for complete search history.

(56) References Cited

U.S. PATENT DOCUMENTS

| | | |
|---|---|---|
| 3,929,992 A | 12/1975 | Sehgal et al. |
| 3,993,749 A | 11/1976 | Sehgal et al. |
| 4,316,885 A | 2/1982 | Rakhit |
| 4,650,803 A | 3/1987 | Stella |
| 4,885,171 A | 12/1989 | Surendra et al. |
| 5,023,263 A | 6/1991 | VonBurg |
| 5,023,264 A | 6/1991 | Caufield |
| 5,078,999 A | 1/1992 | Warner et al. |
| 5,080,899 A | 1/1992 | Sturm et al. |
| 5,100,883 A | 3/1992 | Schichser |
| 5,100,899 A | 3/1992 | Calne |
| 5,118,677 A | 6/1992 | Caufield |
| 5,118,678 A | 6/1992 | Kao |
| 5,120,842 A | 6/1992 | Failli |
| 5,162,333 A | 11/1992 | Failli |
| 5,177,203 A | 1/1993 | Failli |
| 5,206,018 A | 4/1993 | Sehgal et al. |
| 5,221,670 A | 6/1993 | Caufield |
| 5,256,790 A | 10/1993 | Nelson |
| 5,258,389 A | 11/1993 | Goulet |
| 5,260,300 A | 11/1993 | Hu |
| 5,262,423 A | 11/1993 | Kao |
| 5,286,730 A | 2/1994 | Caufield et al. |
| 5,286,731 A | 2/1994 | Caufield et al. |
| 5,288,711 A | 2/1994 | Mitchell et al. |
| 5,302,584 A | 4/1994 | Kao |
| 5,321,009 A | 6/1994 | Baeder et al. |
| 5,362,718 A | 11/1994 | Skotnicki et al. |
| 5,373,014 A | 12/1994 | Failli |
| 5,378,836 A | 1/1995 | Kao |
| 5,385,908 A | 1/1995 | Nelson |
| 5,385,909 A | 1/1995 | Nelson et al. |
| 5,385,910 A | 1/1995 | Ocain |
| 5,387,589 A | 2/1995 | Kulkami |
| 5,389,639 A | 2/1995 | Failli |
| 5,391,730 A | 2/1995 | Skotnicki |
| 5,411,967 A | 5/1995 | Kao |
| 5,434,260 A | 7/1995 | Skotnicki |
| 5,463,048 A | 10/1995 | Skotnicki |
| 5,480,988 A | 1/1996 | Failli |
| 5,480,989 A | 1/1996 | Kao |
| 5,489,680 A | 2/1996 | Failli |
| 5,491,231 A | 2/1996 | Nelson |
| 5,496,832 A | 3/1996 | Armstrong |
| 5,504,091 A | 4/1996 | Molnar-Kimber |
| 5,516,770 A | 5/1996 | Waranis et al. |
| 5,516,781 A | 5/1996 | Morris et al. |
| 5,530,006 A | 6/1996 | Enever et al. |
| 5,536,729 A | 7/1996 | Leonard et al. |
| 5,559,121 A | 9/1996 | Harrison et al. |
| 5,561,138 A | 10/1996 | Annstrong |
| 5,563,145 A | 10/1996 | Failli |
| 5,616,588 A | 4/1997 | Waranis et al. |
| 5,665,772 A | 9/1997 | Cottens |
| 5,674,874 A | 10/1997 | Huasheer |
| 5,780,462 A | 7/1998 | Lee |
| 6,022,852 A | 2/2000 | Klokkers |

(Continued)

FOREIGN PATENT DOCUMENTS

AU 759219 6/2000

(Continued)

OTHER PUBLICATIONS

Notice of Opposition dated Aug. 2, 2011 from corresponding Indian Patent Application No. 1155/KOLNP/2007 generated at the Indian Patent Office, based on the opponent's 2009 filing.
Added Substances (Excipients) in Parenteral Formulations in Modern Pharmaceutics, 4th Ed., Banker & Rhods, Eds., Marcel Dekker Inc.: New York, NY, Jul. 4, 2002, pp. 388-393.
Added Substances in Pharmaceutical Dosage forms and Drug Delivery Systems, 7th Ed., Ansel et al., Eds., Lippincott Williams and Wilkins: Philadelphia, PA, 1999, pp. 405-406.
Baker et al, Rapamycin (AY-22,989), A New Antifungal Antibiotic, III. In Vitro and In Vivo Evaluation, The Journal of Antibiotics, vol. XXXI, No. 6, pp. 539-545, (Jun. 1978).

(Continued)

*Primary Examiner* — Jeffrey S. Lundgren
*Assistant Examiner* — Gregg Polansky
(74) *Attorney, Agent, or Firm* — David A. Rubin; Howson & Howson LLP

(57) ABSTRACT

This invention provides CCI-779 cosolvent concentrates which are useful in preparing a parenteral formulation of rapamycin 42-ester with 3-hydroxy-2-(hydroxymethyl)-2-methylpropionic acid (CCI-779) following admixture with a diluent.

13 Claims, No Drawings

U.S. PATENT DOCUMENTS

| | | | |
|---|---|---|---|
| 6,193,985 B1 | 2/2001 | Sonne | |
| 6,277,983 B1 | 8/2001 | Shaw | |
| 6,358,969 B1 | 3/2002 | Shelley | |
| 6,399,626 B1 | 6/2002 | Zhu | |
| 6,565,859 B1 | 5/2003 | Fricker et al. | |
| 6,605,613 B2 | 8/2003 | Navarro | |
| 6,670,168 B1 | 12/2003 | Katz | |
| 6,670,355 B2 | 12/2003 | Azrolan et al. | |
| 6,677,357 B2 | 1/2004 | Zhu | |
| 6,680,330 B2 | 1/2004 | Fawzi | |
| 6,852,729 B2 | 2/2005 | Navarro et al. | |
| 7,074,804 B2 | 7/2006 | Zhu | |
| 7,153,957 B2 | 12/2006 | Chew | |
| 7,189,735 B2 | 3/2007 | Dukart | |
| 7,202,256 B2 | 4/2007 | Gu et al. | |
| 7,273,874 B2 | 9/2007 | Graziani | |
| 7,276,498 B2 | 10/2007 | Graziani | |
| 7,282,505 B2 | 10/2007 | Zhu | |
| 7,332,601 B2 | 2/2008 | Cai | |
| 7,384,953 B2 | 6/2008 | Shaw | |
| 7,622,578 B2 | 11/2009 | Zhang | |
| 8,026,276 B2 | 9/2011 | Rubino | |

FOREIGN PATENT DOCUMENTS

| | | | |
|---|---|---|---|
| DE | 4418115 A1 | 12/1994 | |
| EP | 0041795 A2 | 12/1981 | |
| EP | 0329460 A2 | 8/1989 | |
| EP | 0525960 A1 | 3/1993 | |
| EP | 0649659 A1 | 4/1995 | |
| EP | 0650730 A1 | 5/1995 | |
| GB | 2327611 A | 2/1999 | |
| WO | WO9319763 | 10/1993 | |
| WO | WO9402136 | 2/1994 | |
| WO | WO9528406 | 10/1995 | |
| WO | WO 9613273 | 5/1996 | |
| WO | WO 9722358 | 6/1997 | |
| WO | WO 9830205 | 7/1998 | |
| WO | WO 9945918 | 9/1999 | |
| WO | WO 9956727 | 11/1999 | |
| WO | WO 0033878 | 6/2000 | |
| WO | WO 0197809 A2 | 12/2001 | |
| WO | WO0240000 | 5/2002 | |
| WO | WO 03/018573 A1 | 3/2003 | |
| WO | WO 03008574 A1 | 3/2003 | |
| WO | WO 03/077915 A1 | 9/2003 | |
| WO | WO 2004011000 | 2/2004 | |
| WO | WO 2005010010 A1 | 2/2005 | |
| WO | WO 2007075621 | 7/2007 | |

OTHER PUBLICATIONS

Butylated Hydroxyanisole in Handbook of Pharmaceutical Excipients, 3rd Ed., Kibbe, Ed., American Pharmaceutical Association: Washington, DC, 2000, pp. 49-50.

Butylated Hydroxytoluene in Handbook of Pharmaceutical Excipients, 3rd Ed., Kibbe, Ed., American Pharmaceutical Association: Washington, DC, 2000, pp. 51-52.

Butylated Hydroxyanisole in RÖmpp Lexikon Chemie, 10th Ed., Falbe and Regitz, Eds., Georg Theime Verlag, Stuttgart, Germany: 1996, p. 423.

Calne et al, Prolonged Survival of Pig Orthotopic Heart Grafts Treated with Cyclosporin A, The Lancet, pp. 1183-1185 (Jun. 3, 1978).

Citric Acid Monohydrate in Handbook of Pharmaceutical Excipients, 3rd Ed., Kibbe, Ed., American Pharmaceutical Association: Washington, DC, 2000, pp. 140-141.

Citric Acid in RÖmpp Lexikon Chemie, 10th Ed. Falbe and Regitz, Eds., Georg theime Verlag, Stuttgart, Germany: 1996, p. 759-760.

Dudkin, Biochemical correlates of mTOR inhibition by the rapamycin ester CCI-779 and tumore growth inhibition, Clinical Cancer Research, 7:1758-1764, (Jun. 2001).

Fiedler, H., Lexikon der Hilfsstoffe fur pharmazie, Kosmetik und angrenzende Gebiete, 2(4):1210-1217, Cantor-Verlag, aulendorf, Deutchland, 1996.

Garber, K., Rapamycin's Resurrection: A new way to target the cancer cell cycle, J. National Cancer Institute, 93(20):1517-1519, (Oct. 2001).

Georger, Antitumor Activity of the rapamycin analog CCI-779 in human primitive neuroectodermal tumor/medulloblastoma models as single agent and in combination therapy, Cancer Research, 61:1527-1532, (Feb. 2001).

Grunwald, V., et al, Inhibitors of mTOR reverse doxorubicin resistance conferred by PTEN status in prostate cancer cells, Cancer Research, 62:6141-6145, Nov. 2002.

Hidalgo et al, A Phase I and Pharmacological study of CCI-779, a rapamycin ester cell cycle inhibitor, annals of oncology, 11(4):133, (Oct. 2000).

Hidalgo et al, The rapamycin-sensitive signal transduction pathway as a target for cancer therapy, Oncogene, 19(56):6680-6686, (Dec. 2000).

Injection-the basis, preparation and application-, Nanzando Edition 1, pp. 21-23, (1995).

Machine Translation of "Butylated Hydroxytoluene" in RÖmpp Lexikon Chemie, 10th Ed., Falbe and Regitz, Eds., Georg Theime Verlag, Stuttgart, Germany: 1996, p. 423.

Machine Translation of "Citric Acid" RÖmpp Lexikon Chemie, 10th Ed., Falbe and Regitz, Eds., Georg Theime Verlag, Stuttgart, Germany: 1996, p. 759-760.

Machine Translation of "Oxidation Inhibitor" in RÖmpp Lexikon Chemie, 10th Ed., Falbe and Regitz, Eds., Georg Theime Verlag, Stuttgart, Germany: 1996, p. 229.

Machine translation of Tocopherol in RÖmpp Lexikon Chemie, 10th Ed., Falbe and Regitz, Eds., Georg Theime Verlag, Stuttgart, Germany: 1996, p. 4572-4573.

Martel et al, Inhibition of the Immune Response by Rapamycin, a New Antifungal Antibiotic, Can. J. Physiol. Pharmacol. vol. 55, pp. 48-51 (1977).

Mendenhall. Stability of parenterals, Drug Development and Industrial Pharmacy, 10(8-9):1297-1342, (Oct. 1984).

Oellerich et al, Immunosuppressive Drug Monitoring of Sirolimus and Cyclosporine in Pediatric Patients, Clinical biochemistry, 37:424-428, (Jun. 2004).

Oxidation Inhibitor in RÖmpp Lexikon Chemie, 10th Ed. Falbe and Regitz, Eds., Georg theime Verlag, Stuttgart, Germany: 1996, p. 229.

Pharmaceutical Additive Dictionary, Yakuji Nippou Limited, pp. 2-3, 6, 38-39, 63, 90-91, 117, 214 (1994).

Podsypanina, K., An inhibitor of mTOR reduces neplasia and normalizes p70/S6 Kinase Actibity in Pten+/− mice, PNAS, 98(18):10320-10325, (Aug. 2001).

Powell, M., Compendium of Excipients for Parenteral Formulations, PDA Journal of Pharmaceutical Science and Technology, 52(5):238-311, (Nov. 1999).

Sehgal et al, Rapamycin (AY-22, 989), A New Antifungal Antibiotic, II. Fennentation, Isolation and Characterization, The Journal of Antibiotics, vol. XXVIII No. 10, pp. 727-732, (Oct. 1975).

Solution Formulations in Pharmaceutical Preformulation and formulation, 196-210, (2001).

Sorbera, L.A. et al, CCI-779 Incolytic mTOR inhibitor, Drugs of the future, 27(1):7-13, (Jan. 2002).

Strickley, R., Parenteral formulations of small molecules therapeutics marketed in the United States (1999) Part I, Journal of Pharmaceutical Science and Technology, 53(6):324-349, (Nov. 1999).

Sweetana, S. and Akers. M., Solubility principles and practices for parenteral rug dosage form development, PDA Journal of Pharmaceutical Science and Technology, 50(5):330-342, Sep. 1996.

Tocopherol in RÖmpp Lexikon Chemie, 10th Ed., Falbe and Regitz, Eds., Georg Theime Verlag, Stuttgart, Germany: 1996, p. 4572-4573.

Vezina et al, Rapamycin (AY-22,989) A new Antifungal Antibiotic, 1. Taxonomy of the Producing Streptomycete and Isolation of the Active Principle, The Journal of Antibiotics, pp. 721-726 (Oct. 1975).

Wyeth Pharmaceuticals Inc. Highlights of Prescribing Information, (Torisel, temsirolimus), Philadelphia, USA (May 2007).

Yu, mTOR, a novel target in breast cancer: the effect of CCI-779, an mTOR inhibitor, in preclinical models of breast cancer, Endocrine-Related Cancer, 8:249-258, (Sep. 2001).

Declaration Under 37 CFR §1.132 filed in parent U.S. Appl. No. 10/626,943, filed Mar. 18, 2011.

Correspondence from the Food and Drug Administration dated May 29, 2012 regarding the New Chemical Entity exclusivity for the Torisel® formulation.

CCI-779 CONCENTRATE FORMULATIONS

CROSS-REFERENCE TO RELATED APPLICATION

This is a divisional of U.S. patent application Ser. No. 10/626,943, filed Jul. 25, 2003, which claims the benefit of U.S. Provisional Patent Application No. 60/399,526, filed Jul. 30, 2002, expired.

BACKGROUND OF THE INVENTION

This invention relates to parenteral formulations of rapamycin 42-ester with 3-hydroxy-2-(hydroxymethyl)-2-methylpropionic acid (CCI-779).

Rapamycin is a macrocyclic triene antibiotic produced by *Streptomyces hygroscopicus*, which was found to have antifungal activity, particularly against *Candida alb cans*, both in vitro and in vivo [C. Vein et al., *J. Antibiot.* 28, 721 (1975); S. N. Sega et al., *J. Antibiot.* 28, 727 (1975); H. A. Baker et al., *J. Antibiot.* 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed. Cyclosporin A and FK-506, other macrocyclic molecules, also have been shown to be effective as immunosuppressive agents, therefore useful in preventing transplant rejection [R. Y. Caine et al., *Lancet* 1183 (1978); and U.S. Pat. No. 5,100,899]. R. Martel et al. [*Can. J. Physiol. Pharmacol.* 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

Rapamycin 42-ester with 3-hydroxy-2-(hydroxymethyl)-2-methylpropionic acid (CCI-779) is ester of rapamycin which has demonstrated significant inhibitory effects on tumor growth in both in vitro and in vivo models. The preparation and use of hydroxyesters of rapamycin, including CCI-779, are disclosed in U.S. Pat. No. 5,362,718.

CCI-779 exhibits cytostatic, as opposed to cytotoxic properties, and may delay the time to progression of tumors or time to tumor recurrence. CCI-779 is considered to have a mechanism of action that is similar to that of sirolimus. CCI-779 binds to and forms a complex with the cytoplasmic protein FKBP, which inhibits an enzyme, mTOR (mammalian target of rapamycin, also known as FKBP 12-rapamycin associated protein [FRAP]) Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G□ to S. The mechanism of action of CCI-779 that results in the GE to S phase block is novel for an anticancer drug.

In vitro, CCI-779 has been shown to inhibit the growth of a number of histologically diverse tumor cells. Central nervous system (CNS) cancer, leukemia (T-cell), breast cancer, prostate cancer, and melanoma lines were among the most sensitive to CCI-779. The compound arrested cells in the G1 phase of the cell cycle.

In vivo studies in nude mice have demonstrated that CCI-779 has activity against human tumor xenografts of diverse histological types. Gliomas were particularly sensitive to CCI-779 and the compound was active in an orthotopic glioma model in nude mice. Growth factor (platelet-derived)-induced stimulation of a human glioblastoma cell line in vitro was markedly suppressed by CCI-779. The growth of several human pancreatic tumors in nude mice as well as one of two breast cancer lines studied in vivo also was inhibited by CCI-779.

A primary obstacle towards the formulation of CCI-779 as a parenteral dosage form is the poor aqueous solubility, which is less than 1 µg/ml. The drug is a non-electrolyte and approaches such as pH adjustment and salt formation are not useful for improving the aqueous solubility. CCI-779 has poor solubility in pharmaceutically acceptable vegetable oils but CCI-779 is soluble in certain water-miscible organic solvents that are acceptable for parenteral administration. These include ethanol, propylene glycol, polyethylene glycol and dimethylacetamide. Two problems or limitations exist with respect to the formulation of CCI-779 in these organic solvents. First, chemical instability has been noted in virtually all solvents. The instability can be due to oxidative degradation of CCI-779 or to cleavage of a lactone bond, resulting in the formation of the ring opened seco-CCI-779. Second, formulations of CCI-779 in organic solvents will precipitate upon dilution with aqueous infusion solutions, such as 0.9% Sodium Chloride Injection or 5% Dextrose Injections, or with blood. This is a primary limitation to the use of water miscible organic solvents, also referred to as cosolvents, when used as vehicles for highly water-insoluble compounds.

SUMMARY OF THE INVENTION

This invention avoids the aforementioned problems by solubilizing CCI-779 with a parenterally acceptable cosolvent accompanied by the presence of an antioxidant and/or chelating agent in the solution. The parenteral formulation contains, in addition, a parenterally acceptable surfactant.

In one aspect, this invention provides a CCI-779 cosolvent concentrate which contains CCI-779, an alcoholic solvent, and an antioxidant.

In another aspect, the invention provides a parenteral formulation containing CCI-779, an alcoholic solvent, an antioxidant, a diluent solvent, and a surfactant.

In yet another aspect, the invention provides a process for preparing a parenteral CCI-779 formulation by mixing CCI-779 with a parenterally acceptable solvent and an antioxidant to provide a cosolvent concentrate; mixing a diluent solvent and a surfactant to produce a diluent; and mixing the cosolvent concentrate with the diluent to provide the CCI-779 parenteral formulation.

Other aspects and advantage of the present invention will be readily apparent from the foregoing detailed description of the invention.

DETAILED DESCRIPTION OF THE INVENTION

Thus, the invention provides a CCI-779 cosolvent concentrate containing an parenterally acceptable solvent and an antioxidant as described above and a parenteral formulation containing CCI-779, composed of CCI-779, an parenterally acceptable cosolvent, an antioxidant, a diluent solvent, and a surfactant.

Any given formulation of this invention may contain multiple ingredients of each class of component. For example, a parenterally acceptable solvent can include a non-alcoholic solvent, an alcoholic solvent, or mixtures thereof. Examples of suitable non-alcoholic solvents include, e.g., dimethylacetamide, dimethylsulfoxide or acetonitrile, or mixtures thereof "An alcoholic solvent," may contain one or more alcohols as the alcoholic solvent component of the formulation. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

In the present invention, the stability of CCI-779 in parenterally acceptable alcoholic cosolvents is enhanced by addition of an antioxidant to the formulation. Acceptable antioxidants include, but are not limited to, citric acid, d,1-α-tocopherol, BHA, BHT, monothioglycerol, ascorbic acid, propyl gallate, and mixtures thereof. Generally, the formulations of the invention will contain an antioxidant component(s) in a concentration ranging from 0.001% to 1% w/v, or 0.01% to 0.5% w/v, of the cosolvent concentrate, although lower or higher concentrations may be desired. Of the antioxidants, d,1-α-tocopherol is particularly desirable and is used at a concentration of 0.01 to 0.1% w/v with a preferred concentration of 0.075% w/v of the cosolvent concentrate.

In certain embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations. Other chelating agents include such materials as are capable of binding metal ions in solution, such as ethylene diamine tetra acetic acid (EDTA), its salts, or amino acids such as glycine are capable of enhancing the stability of CCI-779.

In some embodiments, components with chelating activity are included in the formulations of the invention as the sole "antioxidant component". Typically, such metal-binding components, when acting as chelating agents are used in the lower end of the range of concentrations for the antioxidant component provided herein. In one example, citric acid enhanced the stability of CCI-779 when used at a concentration of less than 0.01% w/v. Higher concentrations are less stable solutions and thus, less desirable for products to be subject to long-term storage in liquid form. Additionally, such chelating agents may be used in combination with other antioxidants as part of the antioxidant component of the invention. For example, an acceptable formulation may contain both citric acid and d,1-α-tocopherol. Optimal concentrations for the selected antioxidant(s) can be readily determined by one of skill in the art, based upon the information provided herein.

Advantageously, in the formulations of the invention, precipitation of CCI-779 upon dilution with aqueous infusion solutions or blood is prevented through the use of a surfactant contained in the diluent solution. The most important component of the diluent is a parenterally acceptable surfactant. One particularly desirable surfactant is polysorbate 20 or polysorbate 80. However, one of skill in the art may readily select other suitable surfactants from among salts of bile acids (taurocholate, glycocholate, cholate, deoxycholate, etc.) which are optionally combined with lecithin. Alternatively, ethoxylated vegetable oils, such as a pegylated castor oil [e.g., such as PEG-35 castor oil which is sold, e.g., under the name Cremophor® EL polyethyleneglycerol triricinoleat 35 (polyethoxy 35 castor oil), BASF], vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60 Other components of the diluent may include water, ethanol, polyethylene glycol 300, polyethylene glycol 400, polyethylene glycol 600, polyethylene glycol 1000, or blends containing one or more of these polyethylene glycols, propylene glycol and other parenterally acceptable cosolvents or agents to adjust solution osmolarity such as sodium chloride, lactose, mannitol or other parenterally acceptable sugars, polyols and electrolytes. It is expected that the surfactant will comprise 2 to 100% w/v of the diluent solution, 5 to 80% w/v, 10 to 75% w/v, 15 to 60% w/v, and preferably, at least 5% w/v, or at least 10% w/v, of the diluent solution.

The parenteral formulation can be prepared as a single solution, or preferably can be prepared as a cosolvent concentrate containing CCI-779, an alcoholic solvent, and an antioxidant, which is subsequently combined with a diluent that contains a diluent solvent and suitable surfactant. Prior to use, the cosolvent concentrate is mixed with a diluent comprising a diluent solvent, and a surfactant. When CCI-779 is prepared as a cosolvent concentrate according to this invention, the concentrate can contain concentrations of CCI-779 from 0.05 mg/mL, from 2.5 mg/mL, from 5 mg/mL, from 10 mg/mL or from 25 mg/mL up to approximately 50 mg/ml. The concentrate can be mixed with the diluent up to approximately 1 part concentrate to 1 part diluent, to give parenteral formulations having concentrations of CCI-779 from 1 mg/mL, from 5 mg/mL, from 10 mg/mL, from 20 mg/mL, up to approximately 25 mg/ml. For example the concentration of CCI-779 in the parenteral formulation may be from about 2.5 to 10 mg/mL. This invention also covers formulations having lesser concentrations of CCI-779 in the cosolvent concentrate, and formulations in which one part of the concentrate is mixed with greater than 1 part of the diluent, e.g., concentrate: diluent in a ratio of about 1:1.5, 1:2, 1:3, 1:4, 1:5, or 1:9 v/v and so on, to CCI-779 parenteral formulations having a CCI-779 concentration down to the lowest levels of detection.

Typically the antioxidant may comprise from about 0.0005 to 0.5% w/v of the formulation. The surfactant may for example comprise from about 0.5% to about 10% w/v of the formulation. The alcoholic solvent may for example comprise from about 10% to about 90% w/v of the formulation.

The parenteral formulations of this invention can be used to produce a dosage form that is suitable for administration by either direct injection or by addition to sterile infusion fluids for intravenous infusion.

The following provide representative examples of the formulations of this invention. The preparation of CCI-779 is described in U.S. Pat. No. 5,362,718, which is hereby incorporated by reference. A regioselective preparation of CCI-779 is described in U.S. Pat. No. 6,277,983, which is hereby incorporated by reference.

When the drug is given by direct injection, a diluent formulation that is primarily aqueous is most suitable, although not required. See, e.g., Example 3. When the drug is administered by addition to sterile infusion solutions, the diluent formulation can be either primarily aqueous, e.g., water, glucose solution, saline, buffered saline, and the like, or non-aqueous. In the latter case a water miscible cosolvent replaces water in the diluent. Example 4 is a formulation that is non-aqueous and is intended to be added to sterile infusion solutions, such as 0.9% sodium chloride injection, 5% dextrose injection, lactated ringers injection, and other commonly used intravenous infusion solutions prior to administration via intravenous infusion.

Cosolvent Concentrate

EXAMPLE 1

| | |
|---|---|
| CCI-779 | 25 mg |
| Citric acid, anhydrous | 0.005% w/v |
| Dehydrated ethanol, USP | q.s. 1.0 ml |

The above formulation was packaged in a glass ampoule with a nitrogen/air headspace and had a shelf-life of 18-30 months when stored at 2-8° C.

EXAMPLE 2

| | |
|---|---|
| CCI-779 | 25 mg |
| dehydrated ethanol, USP | 0.395 g |
| citric acid, anhydrous, USP | 0.025 mg [0.0025% w/v] |
| d,l-α-tocopherol, USP | 0.75 mg [0.075% w/v] |
| propylene glycol, USP | q.s. 1.0 mL |

The above formulation was packaged in a vial with a nitrogen/air headspace. It has demonstrated good stability after 24 months storage at 2-8° C. and room temperature. No significant degradation had been observed after 24 months at 5° C. Both formulations presented in Examples 1 and 2 can be sterilized by aseptic filtration.

Example 3 is a formula that contains a non-alcoholic cosolvent as the primary vehicle:

EXAMPLE 3

| | |
|---|---|
| CCI-779 | 25 mg |
| Citric acid, anhydrous | 0.025 mg |
| D,L-α-tocopherol, USP | 0.75 mg |
| N,N-dimethylacetamide | q.s 1.0 mL |

Exposure to short-term temperature stress indicated that the above formula was stable (greater than 97% potency was retained after exposure to stress temperature conditions (e.g. 70° C.) for at least 24 hours).

Diluents

EXAMPLE 4

| | |
|---|---|
| Polysorbate 80, NF | 5% w/v |
| Polyethylene glycol 400 NF | 5% w/v |
| Water for injection, USP | q.s. 100% |

This formulation can be packaged in vials, sealed and sterilized by autoclaving. The above formulation can be preferably combined in a ratio of 9:1 v/v with the cosolvent concentrate of Example 1 or 2 to produce a solution of CCI-779 at a concentration of 2.5 mg/ml. The resulting mixture can be injected directly or further diluted with 0.9% Sodium Chloride Injection or 5% Dextrose Injection to provide a solution for intravenous infusion. Such mixtures are physically and chemically stable for several hours at room temperature. The above diluent, when combined with the CCI-779 formulations in Examples 1 and 2, have been used to deliver doses of 0.5 to 500 mg CCI-779 via direct intravenous injection or intravenous infusion.

Additional examples of diluent formulas which have a primarily aqueous composition are given below:

EXAMPLE 5

| | |
|---|---|
| Cremophor ® EL (polyethoxy 35 castor oil) | 10 w/v % |
| Water for Injection | q.s. 100 w/v % |

In this example, the diluent was combined with an equal volume of a CCI-779 concentrate (e.g. Example 2 above) to produce a largely aqueous vehicle that was physically stable for several hours at room temperature. This mixture could be suitable for direct intravenous injection.

EXAMPLE 6

| | |
|---|---|
| Vitamin E TPGS NF | 10 w/v % |
| Water for Injection, USP | q.s 100 w/v % |

The above formula was combined with an equal volume of CCI-779 concentrate (e.g. Example 2 above) to produce a largely aqueous vehicle that was physically stable for several hours at room temperature. The resulting concentrate-diluent mixture could also be diluted with 0.9% sodium chloride injection without evidence of drug precipitation. Example 6 is a diluent suitable for direct intravenous injection of CCI-779 (e.g. IV push) or intravenous infusion following dilution in sterile infusion solutions.

EXAMPLE 7

| | |
|---|---|
| Polysorbate 20 | 10% w/v |
| Water for Injection, USP | q.s. 100% w/v |

The diluent in Example 7 was combined with an equal volume of CCI-779 concentrate (e.g. Example 2) to produce a mixture that was physically stable for several hours at room temperature. The concentrate-diluent mixture can be used for administration of CCI-779 via IV push.

EXAMPLE 8

| | |
|---|---|
| Polysorbate 80, NF | 40% w/v |
| Dehydrated ethanol, USP | 19.9% w/v |
| Polyethylene glycol 400, NF | q.s. 100% |

The above formulation was sterilized by aseptic filtration. The above formula can be combined with the cosolvent concentrates of Example 1 or 2 preferably in a volume ratio of 1.5:1 to produce a solution containing 10 mg/ml CCI-779. This can be further diluted with 0.9% Sodium Chloride injection or 5% Dextrose Injection to provide a solution for intravenous infusion. These mixtures are physically and chemically stable for several hours at room temperature. The above diluent, when combined with the CCI-779 formulations in Examples 1 and 2, are useful for delivering doses of 2 to 500 mg via intravenous infusion.

EXAMPLE 9

| | |
|---|---|
| Polysorbate 20 | 20% w/v |
| Polyethylene glycol 400 | q.s 100% w/v |

The above formula was combined with an equal volume of CCI-779 concentrate (e.g. Example 2) to produce a clear mixture. The concentrate-diluent mixture can be diluted with 0.9% sodium chloride injection to produce a mixture that was physically stable for several hours at room temperature. Example 9 can be used to administer CCI-779 via intravenous infusion.

The examples herein illustrate the formulations of the invention and their preparation, but are not limiting. It will be readily understood that other solvents, antioxidants, diluents and/or surfactants can be utilized in the present invention. In addition, numerous modifications to the examples are encompassed by the scope of the following claims. All documents identified herein are incorporated by reference.

What is claimed is:

1. A CCI-779 cosolvent concentrate for preparing a parenteral formulation upon admixture with a diluent, said concentrate comprising:
   about 1 mg/mL to about 25 mg/mL of CCI-779;
   about 15% w/v to about 60% w/v dehydrated ethanol;
   about 15% w/v to about 60% w/v propylene glycol;
   about 0.01% w/v to about 0.1% w/v of d,1-α-tocopherol; and
   about 0.001 to about 0.005% w/v of citric acid.

2. The CCI-779 cosolvent concentrate according to claim 1, wherein the citric acid is about 0.0025% w/v of the cosolvent concentrate.

3. The CCI-779 cosolvent concentrate according to claim 1, wherein the dehydrated ethanol is at least about 30% w/v of the cosolvent concentrate.

4. The CCI-779 cosolvent concentrate according to claim 1, wherein the propylene glycol is about 35% w/v to about 50% w/v of the cosolvent concentrate.

5. The CCI-779 cosolvent concentrate according to claim 1, wherein the d,1-α-tocopherol is about 0.075% of the cosolvent concentrate.

6. The CCI-779 cosolvent concentrate according to claim 1, comprising about 25 mg/mL CCI-779;
   about 40% w/v of dehydrated ethanol;
   about 0.075% w/v of d,1-α-tocopherol;
   about 0.0025% w/v of citric acid; and
   about 35% w/v propylene glycol.

7. The CCI-779 cosolvent concentrate according to claim 1, which is diluted at a ratio of 1:1.5 to 1:2 concentrate to diluent to form the parenteral formulation.

8. A CCI-779 cosolvent concentrate for preparing a parenteral formulation upon admixture with a diluent, said concentrate consisting of about 1 to about 25 mg/mL of CCI-779, about 0.01 to 0.1% w/v of d,1-α-tocopherol, up to about 0.1% w/v of d,1-α-tocopherol, about 0.001 to about 0.005% w/v of citric acid, and about 15 to about 60% w/v of dehydrated ethanol and propylene glycol.

9. The CCI-779 cosolvent concentrate according to claim 8, comprising about 40% w/v dehydrated ethanol.

10. The CCI-779 cosolvent concentrate according to claim 8, comprising about 15% w/v to about 60% w/v propylene glycol.

11. The CCI-779 cosolvent concentrate according to claim 10, comprising about 50% w/v propylene glycol.

12. The CCI-779 cosolvent concentrate according to claim 8, comprising about 0.075% w/v of d,1-α-tocopherol.

13. The CCI-779 cosolvent concentrate according to claim 8, which is diluted at a ratio of 1:1.5 to 1:2 concentrate to diluent to form the parenteral formulation.

* * * * *